United States Patent
Duan et al.

(10) Patent No.: US 6,825,273 B2
(45) Date of Patent: Nov. 30, 2004

(54) POLYMER COMPOSITES CONTAINING ALKYLENE OXIDE COPOLYMERS

(75) Inventors: Robert Duan, Somerset, NJ (US); Darlene Back, Somerville, NJ (US); Alan Theis, Bridgewater, NJ (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 10/362,355

(22) PCT Filed: Apr. 17, 2001

(86) PCT No.: PCT/US01/12475
§ 371 (c)(1),
(2), (4) Date: Feb. 20, 2003

(87) PCT Pub. No.: WO02/22739
PCT Pub. Date: Mar. 21, 2002

(65) Prior Publication Data
US 2004/0127646 A1 Jul. 1, 2004

Related U.S. Application Data

(60) Provisional application No. 60/231,855, filed on Sep. 12, 2000.

(51) Int. Cl.[7] .................................................. C08F 8/00
(52) U.S. Cl. ........................ 525/107; 525/403; 525/404; 525/407; 525/409; 525/523; 526/273
(58) Field of Search ................................. 525/107, 403, 525/404, 407, 409, 523, 416, 108, 116, 120, 122, 22; 526/273

(56) References Cited

U.S. PATENT DOCUMENTS

| | | | |
|---|---|---|---|
| 2,969,403 A | 1/1961 | Frey et al. .................... 260/653 |
| 3,037,943 A | 6/1962 | Hill et al. ........................ 260/2 |
| 3,135,705 A | 6/1964 | Vandenberg .................... 260/2 |
| 3,167,519 A | 1/1965 | Hill et al. ........................ 260/2 |
| 3,219,591 A | 11/1965 | Vandenberg ................. 252/431 |
| 3,403,114 A | 9/1968 | Vandenberg .................... 260/2 |
| 3,932,689 A | * 1/1976 | Watanabe et al. ........... 428/418 |
| 4,193,892 A | 3/1980 | Goeke et al. ................ 252/428 |
| 4,267,309 A | 5/1981 | Goeke et al. ................ 528/413 |
| 4,667,013 A | 5/1987 | Reichle ....................... 528/414 |
| 4,875,287 A | 10/1989 | Creasy et al. ................... 30/34 |
| 5,113,585 A | 5/1992 | Rogers et al. .................. 30/41 |
| 5,326,852 A | 7/1994 | Fujikake et al. ............. 528/414 |
| 5,430,939 A | 7/1995 | Johnston ........................ 30/41 |
| 5,454,164 A | 10/1995 | Yin et al. ....................... 30/41 |
| 5,626,154 A | 5/1997 | Rogers et al. .............. 132/200 |
| 5,956,848 A | 9/1999 | Tseng et al. .................... 30/41 |
| 6,110,483 A | * 8/2000 | Whitbourne et al. ........ 424/423 |
| 6,197,898 B1 | * 3/2001 | van den Berg et al. ...... 525/523 |

OTHER PUBLICATIONS

Chemical Abstract JP 46007709, 1971, Fukul et al.
Chemical Abstract JP 45007751, 1970, Noda et al.
Derwent XP 002181902 & JP 06/073263, Mitsubishi, 15.3, 1994.
Chemical Abstract No. 89420x, JP 46–038695, Mitsui Toatsu, 15.11, 1971.
Chemical Abstract No. 69744, JP 42–018801, Lion Fat & oil Co., 5.10, 1963.
Chemical Abstract No. 89630x, JP 46–038697, Mitsui Toatsu, 15.10, 1968.

* cited by examiner

Primary Examiner—William K. Cheung

(57) ABSTRACT

Polymer composites comprising a water-insoluble polymer and a water-sensitive polymer are disclosed. The water-sensitive polymer is a copolymer polymerized from one or more alkylene oxide monomers and one or more epoxy-functional monomers. The polymer composites can be used in the manufacture of articles having enhanced lubricious-when-wet properties, e.g., wet-shaving devices, and medical devices, e.g., catheters. The articles can provide enhanced retention of lubricity after repeated uses.

24 Claims, No Drawings

POLYMER COMPOSITES CONTAINING ALKYLENE OXIDE COPOLYMERS

This application claims priority of provisional application No. 60/231,855 filed Sep. 12, 2000.

FIELD OF THE INVENTION

The present invention relates to polymer composites. More specifically, the present invention relates to polymer composites comprising a water-insoluble polymer and a water-sensitive alkylene oxide-based copolymer.

BACKGROUND OF THE INVENTION

Water-sensitive polymers, i.e., water-soluble or water swellable, are commonly used in the manufacture of various personal care devices and medical devices which are intended to be used in contact with skin. The water-sensitive polymers function to provide lubricity to the device when it becomes wetted with an aqueous fluid such as water or a body fluid. Typically, the water-sensitive polymers are used in conjunction with water-insoluble polymers which function to provide the appropriate structural characteristics and mechanical integrity to the device for its intended use.

In order to provide an effective combination of a water-sensitive polymer and a water-insoluble polymer for use in making a personal-care device or medical device, it is desirable that the polymers be sufficiently compatible to provide a finished product having a high degree of compositional regularity. That is, when the polymers are not sufficiently compatible, segments of the article may be predominantly comprised of one polymer or the other polymer. This can lead to mechanical failures and to lack of lubricity where desired. Also, it is desirable that the lubricity characteristics are retained after repeated uses of the device.

One common personal care device which typically uses a water-insoluble polymer, e.g., polystyrene, and a water-sensitive polymer, e.g., polyethylene oxide, is a wet-shaving device, i.e., a razor. Typical shaving devices comprise a support structure supporting a blade member and an external skin-engaging portion in proximity to the blade member. The skin-engaging portion typically comprises a composite comprising a matrix of the water-insoluble polymer and the water-sensitive polymer. Polymer compatibilizers, as well as common shaving aids, e.g., vitamin E, aloe or various low-molecular weight polymers, are often included in the composite.

Typical medical devices which can be made lubricious include, for example, catheters, guide wires, endotracheal tubes and implants. Such articles are often comprised of water-insoluble polymers, such as polyethylene, polypropylene, polyvinylchloride and polyurethanes. A variety of approaches to introduce lubricity have been implemented. Coatings of mineral oils, silicone and various water-sensitive polymer coatings have been applied to medical devices to enhance their lubricity. In addition, water-sensitive polymers, such as polyethylene oxide, have been blended and co-extruded with water-insoluble polymers, such as described above, to provide lubricious polymer blends.

Despite the advancements in the art to provide lubricity to polymer devices, a common deficiency is that the devices typically lose their lubricious-when-wet properties after relatively few uses. According to U.S. Pat. No. 5,454,164, a typical shaving device may only retain its lubricious properties for three or four shaves. Accordingly, new polymer composites are desired which can be used to manufacture articles having enhanced lubricity characteristics. In particular, it is desired that such articles significantly retain their lubricity characteristics after repeated uses.

SUMMARY OF THE INVENTION

By the present invention, polymer composites are provided which comprise a water-insoluble polymer and a water-sensitive polymer. The water-sensitive polymer is a copolymer polymerized from one or more alkylene oxide compounds and one or more epoxy-functional compounds.

By virtue of the present invention, it is now possible to manufacture articles having lubricious-when-wet characteristics which can retain their lubricity characteristics after repeated uses. Examples of articles in which the polymer composites of the present invention can be employed include personal care devices, such as shaving devices, and medical devices, such as catheters.

DETAILED DESCRIPTION OF THE INVENTION

As used herein the term "lubricious-when-wet" refers to a reduction in the coefficient of friction of an article upon exposure to water. Details concerning the measurement of an article's coefficient of friction are known to those skilled in the art.

As used herein, the term "water-sensitive" means water-soluble or water-swellable; the term "water-soluble" means that at least 0.2 weight percent, preferably at least 0.5 weight percent, of the polymer is soluble in distilled water (pH=7.0) at 25° C. and 1 atmosphere pressure; and the term "water-swellable" means that the weight of the polymer increases by at least 2 percent, preferably at least 5 weight percent, after being immersed in water at room temperature, e.g., 25° C., for 1 hour.

The particular water-insoluble polymers used in the polymer composites of the present invention are not critical. The water-insoluble polymers can be any polymers which can impart the desired structural characteristics and mechanical integrity to the article in question. Examples of suitable water-insoluble polymers which can be used include polyethylene, polypropylene, polystyrene, butadiene-styrene copolymer (e.g., medium and high impact polystyrene), polyacetal, acrylonitrile-butadiene-styrene copolymer, ethylene vinyl acetate copolymer and blends such as polypropylene/polystyrene blend.

Typically, the water-insoluble polymers are present in the polymer composite in an amount of at least 5 percent, preferably from about 10 to 80 percent, and more preferably from about 20 to 50 percent, based upon the total weight of the polymer composite. Suitable water-insoluble polymers are commercially available. Further details concerning the selection and amounts of the water-soluble polymers are known to those skilled in the art.

The water-sensitive polymers suitable for use in accordance with the present invention are copolymers polymerized from monomers comprising:

(a) an alkylene oxide compound comprising from about 2 to 4 carbon atoms per molecule; and (b) an epoxy-functional compound comprising from about 4 to 25, preferably about 5 to 25 carbon atoms per molecule;

provided, however, that the alkylene oxide compound is not the same compound as the epoxy functional compound.

Preferably, the alkylene oxide compound (also referred to in the art as "alkene oxide" compound) of the present invention is ethylene oxide. The alkylene oxide compound may also be polymerized with one or more polymerizable olefin oxide comonomers in addition to the epoxy-functional compound described hereinafter. The particular olefin oxide comonomer, when used in accordance with the present invention, is not critical and may contain hydrocarbon substituents such as alkyl, cycloalkyl, aromatic, alkene and branched alkyl groups. However, the amount of comonomer, e.g., 1,2-propylene oxide, must not exceed that which would cause the poly(ethylene oxide) to become insoluble or non-swellable in water. Typical olefin oxide comonomers include 1,2-propylene oxide, 2,3-butylene oxide, 1,2-butylene oxide, butadiene monoxide, cyclohexene monoxide, epichlorohydrin, and the like. The preparation of ethylene oxide polymers is disclosed in the literature; see, for example, U.S. Pat. No. 2,969,403, issued to Helmut, et al.; U.S. Pat. No. 3,037,943, issued to Bailey, et al.; U.S. Pat. No. 3,167,519, issued to Bailey, et al.; U.S. Pat. No. 4,193,892, issued to Geoke, et al.; and U.S. Pat. No. 4,267,309, issued to Geoke, et al.

Preferably, the epoxy-functional compounds, i.e., comonomers containing epoxy-functional groups, have one of the structures shown below.

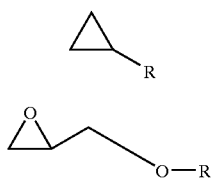

I

II wherein R is a $C_1$ to $C_{25}$ alkyl, $C_1$ to $C_{25}$ hydrocarbon or hetero-hydrocarbon, i.e.; substituted, containing one or more degrees of unsaturation, aryl or alkyl aryl.

Specific examples of some of the I comonomers are 1,2-epoxypropane (propylene oxide); 1,2-epoxybutane; 1,2-epoxypentane; 1,2-epoxyhexane; 1,2-epoxyheptane; 1,2-epoxyoctane; 1,2-epoxynonane; 1,2-epoxydecane; 1,2-epoxydodecane; 1,2-epoxyhexadecane; 1,2-epoxy-3-butene (butadiene monoxide); 1,2-epoxy-4-pentene; 1,2-epoxy-5-hexene; 1,2-epoxy-6-heptene; 1,2-epoxy-7-octene, 1,2-epoxy-9-decene; 2,3-epoxypropylbenzene; and 1,2-epoxyethylbenzene (styrene oxide).

Specific examples of some of the II comonomers are 1,2-epoxy-3-phenoxypropane (glycidyl phenyl ether); 2,3-epoxypropyl methacrylate (glycidyl methacrylate); glycidyl 1,1,2,2-tetrafluoroethyl ether; glycidyl 3-(pentadecadienyl) phenyl ether; 1-allyloxy-2,3-epoxypropane (allyl glycidyl ether); methyl glycidyl ether; n-butyl glycidyl ether; t-butyl glycidyl ether; and tetradecyl glycidyl ether.

Typically, the water-sensitive polymers will be polymerized from about 10 to 99.9, preferably from about 50 to 99.9, and more preferably from about 70 to 99.9 mole percent of the alkylene oxide compound and from about 0.1 to 90, preferably from about 0.1 to 50, and more preferably from about 0.1 to 30 mole percent of the epoxy-functional compound. More than one epoxy-functional compound may be copolymerized with one or more alkylene oxide compounds.

Preferably, the water-sensitive copolymers have a weight average molecular weight greater than about 100,000, more preferably from about 300,000 to 10,000,000 and most preferably from about 1,000,000 to 10,000,000 grams per gram mole ("g/gmole"). Techniques for determining the weight average molecular weight of poly(alkylene oxide) polymers are known to those skilled in the art. One such technique is the gel permeation chromatography.

Typically, the polymer composites of the present invention comprise from about 10 to 99.9 percent, preferably from about 20 to 90 percent, and more preferably from about 50 to 80 percent of the water-sensitive polymer, based on the total weight of the polymer composite. The starting materials suitable for manufacturing the copolymers of the present invention are commercially available.

The particular process used to manufacture the water-sensitive polymers of the present invention is not critical. For example, the polymerization can be conducted in a batch, continuous or semi-continuous mode. See, for example, U.S. Pat. No. 4,667,013 incorporated herein by reference. Typically, the reaction is conducted in a batch reactor in a liquid or slurry phase. The reaction temperature typically ranges from about −25 to 100° C., more typically from about 25 to 65° C., at about atmospheric or above atmospheric pressure, e.g., from about 0.8 to 3 atmospheres to preferably maintain a liquid phase throughout the reaction. A liquid hydrocarbon such as, for example, hexane or isopentane, is typically used to provide the liquid reaction medium through which the alkylene oxide and the epoxy-functional compounds are introduced. Catalysts are preferably used in the preparation of the water-sensitive polymers of the present invention. The process can result in the epoxy-functional compound being block or randomly distributed along the polymer backbone.

The catalysts suitable for preparing the water-sensitive polymers can be any catalyst, or combination of catalysts, which promotes the polymerization of alkylene oxides. One preferred catalyst comprises a reaction product of calcium and ammonia. Catalysts of this type are further described in U.S. Pat. Nos. 4,193,892 and 4,267,309 issued to Goeke, et al., and U.S. Pat. No. 4,667,013 issued to Reichle. Another preferred catalyst comprises an organo zinc compound such as, for example, diethyl zinc, e.g., diethyl zinc and water or an alcohol. Catalysts of this type are further described for example, in U.S. Pat. No. 5,326,852, issued to Masato et al. and Japanese Patent Nos. JP 46007709, JP 45007751 and JP 5302731. Still another preferred catalyst is an aluminum-based catalyst, known as Vandenberg catalysts. Catalysts of this type are further described for example, in U.S. Pat. Nos. 3,135,705, 3,219,591 and 3,403,114 issued to E. J. Vandenberg et al. Further details concerning suitable catalysts are known to those skilled in the art.

Further details concerning suitable processes for preparing the water-sensitive polymers of the present invention are known to those skilled in the art. Moreover, the polymers can be prepared using conventional apparatus known to those skilled in the art.

In addition to the water-sensitive polymer and water-insoluble polymer, additional polymers and other ingredients known to those skilled in the art can be added to the polymer composites of the present invention. Typical polymers and substances include, for example, other water-soluble polymers such as, for example, polyvinyl pyrrolidone, polyacrylamide, hydroxypropyl cellulose, polyvinyl imidazoline, and polyhydroxyethylmethacrylate; hair softeners; oils such as silicone oil and mineral oil; substances that enhance the healing or stop the bleeding of the skin; essential oils such as menthol, eugenol, eucalyptol, safrol, and methyl salicylate; rinsing aids; non-volatile cooling agents; inclusion complexes of skin-soothing agents with cyclodextrin; fragrances; vitamin E (including common forms of vitamin E such as vitamin E acetate); vitamin A and B-carotene; panthenol and aloe; therapeutic agents; antipruritic/counterirritant materials; antimicrobial/keratolytic materials; anti-inflammatory agents; and astringents. The amount of such other polymers and ingredients is dependent upon the particular article to be manufactured. For example, another water-soluble polymer may be present in an amount from about 20 to 80 weight percent, whereas an additive such as vitamin E may be present in an amount of only from about 0.01 to about 5.0 weight percent for example. Further details concerning the selection and amounts of other polymers and ingredients useful in the polymer composites of the present invention can be determined by those skilled in the art.

The polymer composites of the present invention are typically prepared in solid form. Often the composites are prepared as a physical mixture of the water-insoluble polymer and the water-sensitive polymer. The physical mixture may be prepared, for example, in the form of tablets, pellets, powder, granules or extrudate. Often the water-sensitive polymer and water-insoluble polymer are extruded, i.e., melt-blended. One preferred method for manufacturing the polymer composites of the present invention is by the extrusion molding of the polymers at a temperature of from about 250 to 500° F. and a pressure of from about 7000 to 20,000 psig. Further details concerning the processes and equipment suitable for manufacturing the polymer composites of the present invention are known to those skilled in the art.

The particular articles manufactured from the polymer composites of the present invention are not critical. Usually, it is desirable that the articles have lubricious-when-wet characteristics. Preferably, the polymer composites comprise an effective amount of the water-sensitive polymer to provide the desired lubricious-when-wet characteristics. Preferably, in accordance with the present invention, the articles may be used repeatedly, e.g., at least about four times, preferably at least about five times, and more preferably at least about ten times, without a significant reduction in its lubricity characteristics. As used herein, the term "significant reduction in lubricity" means an increase in the coefficient of friction of at least about 50 percent, preferably 100 percent and more preferably 200 percent compared to the coefficient of friction measured during the first usage of the article.

Typical personal-care devices which can be manufactured from the polymer composites of the present invention include, for example, wet shaving devices; i.e., razors. Typical wet-shaving devices comprise a support structure supporting a blade member and an external skin-engaging portion adjacent to the blade member. Examples of wet-shaving devices having lubricious-when-wet characteristics are disclosed for example in U.S. Pat. No. 4,875,287, issued Oct. 24, 1989; U.S. Pat. No. 5,113,585, issued May 19, 1992; U.S. Pat. No. 5,430,939, issued Jul. 11, 1995; U.S. Pat. No. 5,454,164, issued Oct. 3, 1995; U.S. Pat. No. 5,626,154, issued May 6, 1997; and U.S. Pat. No. 5,956,848, issued Sep. 28, 1999, the disclosures of which are incorporated by reference. Further details concerning the manufacture of personal-care devices in which the polymer composites of the present invention can be used are known to those skilled in the art.

Typical medical devices which can be manufactured from the polymer composites of the present invention include, for example, catheters, balloon catheters, guide wires, endotracheal tubes and implants. Further details concerning medical devices in which the polymer composites of the present invention can be used are known to those skilled in the art.

EXAMPLES

The following examples are provided for illustrative purposes and are not intended to limit the scope of the claims which follow.

Example 1

Process for the Preparation of Ethylene Oxide and 1,2-Epoxyphenoxypropane Copolymer The catalysts used herein were prepared according to the procedures outlined in U.S. Pat. Nos. 4,193,892 and 4,267,309 issued to Goeke et al.

Polymerization was carried out in a nitrogen filled dry glass reactor equipped with a condenser, addition funnel and stirrer. The condenser and addition funnel were cooled with a dry ice/isopropanol bath. 700 milliliters ("ml") of hexane was charged into the reactor and the reactor temperature was raised to 50° C. An amount of 6.5 grams of the catalyst slurry were added into the reactor. An amount of 7.4 grams of the 1,2-epoxyphenoxypropane were charged into the reactor while vigorously stirring. Immediately following this addition, 100 grams of ethylene oxide were charged into the addition funnel and slowly added into the reactor over a period of 1.5 to 2 hours. The unreacted ethylene oxide was then vented by purging $CO_2$ into the reaction mixture. The precipitated copolymer was collected by vacuum filtration. The copolymer was washed with 300 ml hexane to remove unreacted monomer and dried under a continuous flow of nitrogen at room temperature overnight. This yielded 123.5 grams of the copolymer. Further analysis by nuclear magnetic resonance spectroscopy ("NMR") showed 2 mole percent incorporation of the 1,2-epoxyphenoxypropane comonomer. Differential scanning calorimetry ("DSC") showed the melting point of the copolymer to be 51.3 with the percent crystallinity of 49.9. Gel permeation chromatography ("GPC") determined weight average molecular weight was 3.05 million.

Examples 2 to 5

Preparation of Other Copolymers

Using the polymerization process as illustrated in the Example 1, a variety of copolymers were synthesized using different comonomers at various loading levels. Table 1. lists the reaction conditions for Examples 2 to 5. Table 2. lists the copolymer characterization results.

TABLE 1

| | Reaction Conditions. | | | | | |
|---|---|---|---|---|---|---|
| Example | Reaction Temp (° C.) | Catalyst (g) | Ethylene Oxide ("EO") (g) | Comonomer | Comonomer (g) | Yield (g) |
| 2 | 50 | 7.5 | 100 | 1,2-epoxyphenoxypropane | 14.4 | 120 |
| 3 | 50 | 6 | 45 | 1,2-epoxyphenoxypropane | 15 | 54 |

TABLE 1-continued

Reaction Conditions.

| Example | Reaction Temp (° C.) | Catalyst (g) | Ethylene Oxide ("EO") (g) | Comonomer | Comonomer (g) | Yield (g) |
|---|---|---|---|---|---|---|
| 4 | 38 | 7.9 | 92.4 | 1,2-epoxybutane | 7.4 | 97.3 |
| 5 | 38 | 8.5 | 92.4 | 1,2-epoxybutane | 14.4 | 107 |

TABLE 2

Copolymers characterization results.

| Example | Comonmer loading % | Melting Point $T_m$ (° C.) | Crystallinity % | Molecular Weight "M.W." × $10^6$ |
|---|---|---|---|---|
| 2 | 5 | 49.0 | 43.1 | 3.65 |
| 3 | 10 | 44.0 | 23.5 | 3.68 |
| 4 | 1.7 | 55.9 | 49.6 | 3.61 |
| 5 | 8.5 | 52.2 | 35.5 | 3.98 |

Examples 6–14

Melt Blending of Polymer Composite

Polymer blends of water-insoluble polymer and the water-sensitive coopolymers prepared in the Examples 1 to 5 were made by mixing the two polymer powders together. Different blends were prepared as set forth in Table 3.

TABLE 3

Polymer Blends.

| Example No. | Water-Sensitive Polymer | Weight % | Water-insoluble Polymer | Weight % |
|---|---|---|---|---|
| 6 | PEO [1] | 70 | Polystyrene | 30 |
| 7 | Example 1 | 70 | Polystyrene | 30 |
| 8 | Example 2 | 70 | Polystyrene | 30 |
| 9 | Example 3 | 70 | Polystyrene | 30 |
| 10 | Example 4 | 70 | Polystyrene | 30 |
| 11 | Example 5 | 70 | Polystyrene | 30 |
| 12 | — | — | Polystyrene | 100 |
| 13 | Example 4 | 100 | — | — |
| 14 | Example 4 | 70 | Polyethylene | 30 |

[1] Contains 60% Union Carbide POLYOX ® WSR-Coag and 40% Union Carbide POLYOX ® WSR-N750 (polyethylene oxide).

To form the polymer composite, 30 grams of the powder were placed in a mixing bowl (C. W. Brabender, Prep Center, Type D-51). The temperature was gradually increased to 120° C. and stirred at 30 rpm for 5 minutes to melt the polymer mixture. This molten polymer mix was then transferred to an 8"×8" mold. The mold was placed into a steam press (Greenerd, Model CPA-60) and pressed at 180° C. for 2 minutes at low pressure (1000 psi). The pressure was increased to 2800 psi (gauge) for 3 minutes while the temperature was maintained at 180° C. The mold was opened after returning to low pressure and cooled with water for 10 minutes.

Example 15

Friction Coefficient Measurements

The polymer blends listed in Table 3. were used in these experiments. The dynamic friction coefficients were measured on a friction coefficient tester manufactured by Kayness Inc. The instrument was equipped with a Chatillon digital force gauge. An analog chart recorder was connected to the force gauge to record the force in real time. The chart recorder was calibrated by the known weights connected to the force gauge. The substrate comprised a moving stainless steel panel having a speed of about 8 inches per minute. To test the lubricity of the lubricious composite, an 8"×1" polymer strip was attached to the substrate using a double-sided tape. The force gauge was connected horizontally to a 210 gram 2"×2" weight. Water was sprayed onto the polymer strip and 15 seconds of hydration time was allowed before the friction measurements. Then the weight was added to one end of the sample and dragged across the 8" long polymer strip. The friction coefficient was calculated from the readings on the force gauge divided by the applied weight. Table 5 summarizes the friction coefficients of the polymer blends.

TABLE 5

Friction Coefficients.

| Example No. | Friction |
|---|---|
| 6 | 0.055 |
| 7 | 0.045 |
| 8 | 0.036 |
| 9 | 0.031 |
| 10 | 0.071 |
| 11 | 0.052 |
| 12 | 0.129 |
| 13 | 0.038 |
| 14 | 0.052 |

Compared with 100% polystyrene (Example 12), most of the blends containing PEO or PEO copolymers showed reduced friction coefficients under hydration. The 70/30 blend of PEO/PS showed a friction coefficient of 0.055. For the poly (ethylene oxide-co-1,2-epoxyphenoxypropane), called P(EO+EPP), copolymers, when the EPP comonomer mole percent loading increased from 2 to 10, the friction coefficient decreased from 0.045 to 0.031 (Example 7, 8 and 9). Similar results were found for the poly(ethylene oxide-co-butylene oxide), called P(EO+BO), copolymers (Examples 11 and 12). As the BO comonomer loading increased from 1.7 to 8.5, the friction coefficient decreased from 0.0712 to 0.052. These results indicate that higher loading of comonomers resulted in lower friction coefficients. As an example, when compared to the Example 6 which used homo PEO polymer, Example 9, which used 10 mole % of the ethylene oxide and 1,2-epoxyphenoxypropane comonomer, reduced the friction by about 44%.

Polyethylene can also be blended with the PEO copolymers to form lubricious-when-wet compositions. 30/70 blend of PE/P(EO+BO), Example 14, had the same friction coefficient as the 30/70 PS/P(EO+BO) Example 11.

Pure PEO copolymers, i.e., 100% are also very effective lubricious-when-wet materials. For example, the 100% P(EO+BO) copolymer (Example 13) showed a low friction coefficient (0.038). However, these polymers were difficult to handle due to their lack of mechanical strength after hydration.

Example 16

Retention of Lubricity

This test was used to simulate a use condition of the lubricious-when-wet compositions where repeated use and long lasting lubricity is desired.

The tests were run according to the following procedure. The friction tester described in the Example 15 was employed to make the measurements. First water was sprayed onto the polymer strip and the strip was allowed to hydrate for 15 seconds. The friction test was carried out and the average dynamic friction was recorded as pass 1. The water was then wiped off using a paper towel and the polymer strip was placed in a 50° C. oven for 1 hour to dry. The strip was cooled to room temperature and then used again to record the average dynamic friction for the second pass. The third, fourth and fifth passes were done in the same way. The cleaning and drying of the polymer strips were carried out between each pass to simulate the repeated use of the strip. The results are summarized in Table 6.

TABLE 6

Abrasion Test Results.

| Pass | Example 6 Friction Coeff. | Example 8 Friction Coeff. |
|---|---|---|
| 1 | 0.055 | 0.036 |
| 2 | 0.077 | 0.041 |
| 3 | 0.095 | 0.048 |
| 4 | 0.101 | 0.057 |
| 5 | 0.159 | 0.065 |
| 6 | 0.178 | 0.078 |

Example 6 which used a PEO homopolymer showed a dramatic increase in the friction coefficient after every wet-dry cycle. After the $6^{th}$ pass, the friction was over 300% that of the new strip. In fact, after 4 passes, its friction coefficient was already higher than pure polystyrene. This is caused by the increased surface roughness after the PEO was released from the strip. This observation was in agreement with the disclosure of U.S. Pat. No. 4,454,164 which indicates that when a PS/PEO-based lubricating strip was used on razor cartridges, after the first 3 to 4 shaves, the lubricious nature of the strip no longer exists.

On the other hand Example 8, which used PEO copolymer, showed better resistance to abrasion. After the $6^{th}$ pass, the friction was approximately equal to the friction experienced on the $2^{nd}$ pass of Example 6. This clearly illustrates that the PEO copolymers can improve the useful life of the lubricating compositions, especially for applications requiring repeated uses.

Although the invention has been described with respect to specific aspects, those skilled in the art will recognize that other aspects are included within the scope of the claims which follow. For example, in addition to the specific epoxide-functional compounds described herein, those skilled in the art will recognize that other epoxide-functional compounds such as, for example, diepoxides, can be used as comonomers with the alkylene oxide compounds of the present invention.

What is claimed is:

1. A personal care or medical device manufactured from a polymer composite comprising a water-insoluble polymer and a water-sensitive polymer; characterized in that the water-sensitive polymer is a copolymer of:
    (a) at least one alkylene oxide compound comprising from about 2 to 4 carbon atoms per molecule; and
    (b) at least one epoxy-functional compound comprising from about 4 to 25 carbon atoms per molecule;
provided that the alkylene oxide compound is not the same compound as the epoxy-functional compound.

2. The device of claim 1 wherein the water-sensitive polymer has a weight average molecular weight of at least 100,000 g/gmole.

3. The device of claim 2 wherein the water-sensitive polymer has a weight average molecular weight of from about 1,000,000 to 10,000,000 g/gmole.

4. The device of claim 1 wherein the alkylene oxide compound is selected from the group consisting of ethylene oxide, propylene oxide, butylene oxide and mixtures thereof.

5. The device of claim 1 wherein the epoxy-functional compound is a monoepoxide or a diepoxide.

6. The device of claim 5 wherein the epoxy-functional compound is selected from the group consisting of epihalohydrins, olefin oxides, epoxy alkyl ethers, and mixtures thereof.

7. The device of claim 1 wherein the copolymer is polymerized from (a) about 10 to 99.9 mole percent of the alkylene oxide compound and (b) about 0.1 to 90 mole percent of the epoxy-functional compound, based on the total mole of the copolymer.

8. The device of claim 1 wherein the water-insoluble polymer is selected from the group consisting of polyethylene, polypropylene, polystyrene, butadiene-styrene copolymer, polyacetal, acetonitrile-butadiene-styrene copolymer, ethylene vinyl acetate copolymer and mixtures thereof.

9. The device of claim 8 wherein the water-insoluble polymer is polystyrene.

10. The device of claim 1 which is a personal care device.

11. The device of claim 10 which is a shaving device.

12. The device of claim 1 which is a medical device.

13. The device of claim 12 wherein the medical device is selected from the group consisting of catheters, balloon catheters, guide wires, endotracheal tubes and implants.

14. The device of claim 1 wherein the polymer composite comprises from about 50 to 99.9 percent of the water-sensitive polymer, based on the total weight of the polymer composite.

15. The device of claim 14 wherein the polymer composite comprises from about 50 to 80 percent of the water-sensitive polymer, based on the total weight of the polymer composite.

16. A polymer composite comprising a water-insoluble polymer and a water-sensitive polymer; characterized in that the water-sensitive polymer is a copolymer of:
    (a) at least one alkylene oxide compound comprising from about 2 to 4 carbon atoms per molecule; and
    (b) at least one epoxy-functional compound comprising from about 4 to 25 carbon atoms per molecule;
provided that the alkylene oxide compound is not the same compound as the epoxy-functional compound, and the polymer composite comprises from about 50 to 99.9 percent of the water-sensitive polymer, based on the total weight of the polymer composite.

17. The polymer composite of claim 16 comprising from about 50 to 80 percent of the water-sensitive polymer, based on the total weight of the polymer composite.

18. The polymer composite of claim 16 wherein the water-sensitive polymer has a weight average molecular weight of from about 1,000,000 to 10,000,000 g/gmole.

19. The polymer composite of claim 16 wherein the alkylene oxide compound is selected from the group consisting of ethylene oxide, propylene oxide, butylene oxide and mixtures thereof.

20. The polymer composite of claim 16 wherein the epoxy-functional compound is a monoepoxide or a diepoxide.

21. The polymer composite of claim 16 wherein the epoxy-functional compound is selected from the group consisting of epihalohydrins, olefin oxides, epoxy alkyl ethers, and mixtures thereof.

22. The polymer composite of claim 16 wherein the copolymer is polymerized from (a) about 10 to 99.9 mole percent of the alkylene oxide compound and (b) about 0.1 to 90 mole percent of the epoxy-functional compound, based on the total mole of the copolymer.

23. The polymer composite of claim 16 wherein the water-insoluble polymer is selected from the group consisting of polyethylene, polypropylene, polystyrene, butadiene-styrene copolymer, polyacetal, acetonitrile-butadiene-styrene copolymer, ethylene vinyl acetate copolymer and mixtures thereof.

24. The polymer composite of claim 23 wherein the water-insoluble polymer is polystyrene.

* * * * *